(12) United States Patent
Bernero et al.

(10) Patent No.: US 7,776,085 B2
(45) Date of Patent: *Aug. 17, 2010

(54) KNEE PROSTHESIS WITH CERAMIC TIBIAL COMPONENT

(75) Inventors: John P. Bernero, Round Rock, TX (US); Ashok C. Khandkar, Salt Lake City, UT (US); Ramaswamy Lakshminarayanan, Salt Lake City, UT (US); Aaron A. Hofmann, Salt Lake City, UT (US)

(73) Assignee: Amedica Corporation, Salt Lake City, UT (US)

( * ) Notice: Subject to any disclaimer, the term of this patent is extended or adjusted under 35 U.S.C. 154(b) by 804 days.

This patent is subject to a terminal disclaimer.

(21) Appl. No.: 11/223,376

(22) Filed: Sep. 8, 2005

(65) Prior Publication Data

US 2006/0052875 A1 Mar. 9, 2006

Related U.S. Application Data

(60) Continuation-in-part of application No. 11/139,280, filed on May 27, 2005, now abandoned, which is a continuation-in-part of application No. 10/987,415, filed on Nov. 12, 2004, which is a division of application No. 10/171,376, filed on Jun. 13, 2002, now Pat. No. 6,881,229, application No. 11/139,280, filed on Jan. 20, 2005, which is a continuation-in-part of application No. 11/040,477, filed on Jan. 20, 2005, which is a continuation-in-part of application No. 10/137,106, filed on Apr. 30, 2002, now Pat. No. 6,846,327.

(60) Provisional application No. 60/287,824, filed on May 1, 2001, provisional application No. 60/289,669, filed on May 8, 2001.

(51) Int. Cl.
*A61F 2/24* (2006.01)

(52) U.S. Cl. .................................... 623/2.32
(58) Field of Classification Search .............. None
See application file for complete search history.

(56) References Cited

U.S. PATENT DOCUMENTS 3,867,728 A 2/1975 Stubstad et al.

(Continued)

FOREIGN PATENT DOCUMENTS

| EP | 0821922 | 2/1998 |
| WO | WO 96/40020 | 12/1996 |
| WO | WO 99/20208 | 4/1999 |
| WO | WO 99/47471 | 9/1999 |

(Continued)

OTHER PUBLICATIONS

International Search Report for PCT/US02/13654, Sep. 11, 2002, 2 pgs.

(Continued)

*Primary Examiner*—David Isabella
*Assistant Examiner*—Jonathan Stroud
(74) *Attorney, Agent, or Firm*—Mintz, Levin, Cohn, Ferris, Glovsky & Popeo P.C.

(57) ABSTRACT

An improved knee prosthesis includes a ceramic tibial component for articulation with natural or prosthetic (re-surfaced) femoral surfaces. The ceramic tibial component is provided in the form of a ceramic monoblock adapted for fixation relative to the patient's tibial bone, or alternately in the form of a ceramic bearing insert component carried by a tibial baseplate member which is adapted in turn for fixation relative to tibial bone. In either form, the ceramic tibial component includes at least one upwardly concave articulation surface for movable bearing engagement by a generally convex or condylar shaped femoral articulation surface. The ceramic tibial component provides improved wear characteristics with extended service life.

35 Claims, 6 Drawing Sheets

U.S. PATENT DOCUMENTS

| | | |
|---|---|---|
| 4,072,532 A | 2/1978 | Fletcher et al. |
| 4,327,449 A | 5/1982 | Charnley |
| 4,695,282 A | 9/1987 | Forte et al. |
| 4,743,256 A | 5/1988 | Brantigan |
| 4,759,766 A | 7/1988 | Buettner-Janz et al. |
| 5,098,449 A * | 3/1992 | Hwang et al. .................. 51/307 |
| 5,152,791 A | 10/1992 | Hakamatsuka et al. |
| 5,158,726 A | 10/1992 | Saita et al. |
| 5,192,327 A | 3/1993 | Brantigan |
| 5,310,408 A | 5/1994 | Schryver et al. |
| 5,314,477 A | 5/1994 | Marnay |
| 5,330,533 A | 7/1994 | Walker |
| 5,401,269 A | 3/1995 | Buettner-Janz et al. |
| 5,425,772 A | 6/1995 | Brantigan |
| 5,462,563 A | 10/1995 | Shearer et al. |
| 5,464,440 A | 11/1995 | Johansson |
| 5,525,557 A | 6/1996 | Pujari et al. |
| 5,549,704 A | 8/1996 | Sutter |
| 5,556,815 A | 9/1996 | Boberski |
| 5,609,635 A | 3/1997 | Michelson |
| 5,641,323 A | 6/1997 | Caldarise |
| 5,697,980 A | 12/1997 | Otani et al. |
| 5,702,449 A | 12/1997 | McKay |
| 5,702,453 A | 12/1997 | Rabbe et al. |
| 5,702,458 A | 12/1997 | Burstein et al. |
| 5,776,199 A | 7/1998 | Michelson |
| 5,782,832 A | 7/1998 | Larsen et al. |
| 5,785,710 A | 7/1998 | Michelson |
| 5,824,100 A | 10/1998 | Kester et al. |
| 5,826,586 A | 10/1998 | Mishra et al. |
| 5,861,041 A | 1/1999 | Tienboon |
| 5,871,546 A | 2/1999 | Colleran et al. |
| 5,871,547 A | 2/1999 | Abouaf et al. |
| 5,879,404 A | 3/1999 | Bateman et al. |
| 5,879,407 A | 3/1999 | Waggener |
| 5,888,222 A | 3/1999 | Coates et al. |
| 5,888,223 A | 3/1999 | Bray |
| 5,899,939 A | 5/1999 | Boyce et al. |
| 5,904,720 A | 5/1999 | Farrar et al. |
| 5,908,796 A | 6/1999 | Pujari et al. |
| 6,013,591 A | 1/2000 | Ying et al. |
| 6,033,438 A | 3/2000 | Bianchi et al. |
| 6,037,519 A | 3/2000 | McKay |
| 6,039,762 A | 3/2000 | McKay |
| 6,039,763 A | 3/2000 | Shelokov |
| 6,069,295 A | 5/2000 | Leitao |
| 6,090,144 A * | 7/2000 | Letot et al. ............... 623/20.34 |
| 6,110,205 A | 8/2000 | Nies |
| 6,113,637 A | 9/2000 | Gill et al. |
| 6,123,729 A | 9/2000 | Insall et al. |
| 6,133,180 A | 10/2000 | Miyake et al. |
| 6,136,029 A | 10/2000 | Johnson et al. |
| 6,136,369 A | 10/2000 | Leitao et al. |
| 6,139,585 A | 10/2000 | Li |
| 6,143,032 A | 11/2000 | Schafer et al. |
| 6,149,686 A | 11/2000 | Kuslich et al. |
| 6,149,688 A | 11/2000 | Brosnahan et al. |
| 6,152,960 A | 11/2000 | Pappas |
| 6,156,069 A | 12/2000 | Amstutz |
| 6,179,874 B1 | 1/2001 | Cauthen |
| 6,187,701 B1 | 2/2001 | Sekino et al. |
| 6,210,612 B1 | 4/2001 | Pickrell et al. |
| 6,235,665 B1 | 5/2001 | Pickrell et al. |
| 6,245,108 B1 | 6/2001 | Biscup |
| 6,261,322 B1 | 7/2001 | Despres, III et al. |
| 6,261,586 B1 | 7/2001 | McKay |
| 6,277,149 B1 | 8/2001 | Boyle et al. |
| 6,281,264 B1 | 8/2001 | Salovey et al. |
| 6,296,667 B1 | 10/2001 | Johnson et al. |
| 6,302,913 B1 | 10/2001 | Ripamonti et al. |
| 6,322,895 B1 | 11/2001 | Canham |
| 6,344,061 B1 | 2/2002 | Leitao et al. |
| 6,346,123 B1 | 2/2002 | McKay |
| 6,368,350 B1 | 4/2002 | Erickson et al. |
| 6,371,988 B1 | 4/2002 | Pafford et al. |
| 6,376,573 B1 | 4/2002 | White et al. |
| 6,398,811 B1 | 6/2002 | McKay |
| 6,436,137 B2 | 8/2002 | Wang et al. |
| 6,447,547 B1 | 9/2002 | Michelson |
| 6,478,823 B1 | 11/2002 | Michelson |
| 6,494,883 B1 | 12/2002 | Ferree |
| 6,494,915 B1 | 12/2002 | Villar Gonzalez et al. |
| 6,494,917 B1 | 12/2002 | McKellop et al. |
| 6,511,510 B1 | 1/2003 | de Bruijn et al. |
| 6,517,580 B1 | 2/2003 | Ramadan et al. |
| 6,527,810 B2 | 3/2003 | Johnson et al. |
| 6,540,785 B1 | 4/2003 | Gill et al. |
| 6,540,787 B2 | 4/2003 | Biegun et al. |
| 6,551,995 B1 | 4/2003 | Oppermann et al. |
| 6,569,201 B2 | 5/2003 | Moumene et al. |
| 6,587,788 B1 | 7/2003 | Green |
| 6,610,097 B2 | 8/2003 | Serbousek et al. |
| 6,641,617 B1 | 11/2003 | Merrill et al. |
| 6,673,075 B2 | 1/2004 | Santilli |
| 6,676,703 B2 | 1/2004 | Biscup |
| 6,706,068 B2 | 3/2004 | Ferree |
| 6,719,794 B2 | 4/2004 | Gerber et al. |
| 6,723,097 B2 | 4/2004 | Fraser et al. |
| 6,736,849 B2 | 5/2004 | Li et al. |
| 6,740,118 B2 | 5/2004 | Eisermann et al. |
| 6,758,849 B1 | 7/2004 | Michelson |
| 6,790,233 B2 | 9/2004 | Brodke et al. |
| 6,818,020 B2 | 11/2004 | Sun et al. |
| 6,827,740 B1 | 12/2004 | Michelson |
| 6,846,327 B2 | 1/2005 | Khandkar et al. |
| 6,881,229 B2 * | 4/2005 | Khandkar et al. ......... 623/23.56 |
| 6,908,484 B2 | 6/2005 | Zubok et al. |
| 6,972,037 B2 | 12/2005 | Zubok et al. |
| 6,972,038 B2 | 12/2005 | Zubok et al. |
| 6,989,030 B1 | 1/2006 | Ohgushi |
| 6,994,728 B2 | 2/2006 | Zubok et al. |
| 6,994,729 B2 | 2/2006 | Zubok et al. |
| 6,997,954 B2 | 2/2006 | Zubok et al. |
| 6,997,955 B2 | 2/2006 | Zubok et al. |
| 7,051,417 B2 | 5/2006 | Michelson |
| 7,066,961 B2 | 6/2006 | Michelson |
| RE39,196 E | 7/2006 | Ying et al. |
| 7,105,030 B2 | 9/2006 | Despres, III et al. |
| 7,115,143 B1 | 10/2006 | Michelson |
| 7,166,129 B2 | 1/2007 | Michelson |
| 2002/0062154 A1 | 5/2002 | Ayers |
| 2002/0111680 A1 | 8/2002 | Michelson |
| 2002/0143403 A1 | 10/2002 | Vaidyanathan et al. |
| 2003/0050709 A1 | 3/2003 | Noth et al. |
| 2003/0153984 A1 | 8/2003 | Khandkar et al. |
| 2003/0233146 A1 | 12/2003 | Grinberg et al. |
| 2004/0024462 A1 | 2/2004 | Ferree et al. |
| 2004/0133281 A1 | 7/2004 | Khandkar et al. |
| 2004/0143332 A1 | 7/2004 | Krueger et al. |
| 2004/0172135 A1 | 9/2004 | Mitchell |
| 2004/0176772 A1 | 9/2004 | Zubok et al. |
| 2004/0176845 A1 | 9/2004 | Zubok et al. |
| 2004/0220679 A1 | 11/2004 | Diaz et al. |
| 2004/0225365 A1 | 11/2004 | Eisermann et al. |
| 2004/0243241 A1 | 12/2004 | Istephanous et al. |
| 2005/0055098 A1 | 3/2005 | Zdeblick et al. |
| 2005/0060040 A1 | 3/2005 | Auxepaules et al. |
| 2005/0079200 A1 | 4/2005 | Rathenow et al. |
| 2005/0090903 A1 * | 4/2005 | Khandkar et al. ......... 623/22.15 |
| 2005/0107888 A1 * | 5/2005 | Khandkar et al. ......... 623/23.39 |
| 2005/0177238 A1 | 8/2005 | Khandkar et al. |
| 2005/0177240 A1 | 8/2005 | Blain |
| 2005/0216092 A1 | 9/2005 | Marik et al. |
| 2005/0273176 A1 * | 12/2005 | Ely et al. .................. 623/22.32 |

| | | | |
|---|---|---|---|
| 2006/0052875 | A1 | 3/2006 | Bernero et al. |
| 2006/0142862 | A1 | 6/2006 | Diaz et al. |

FOREIGN PATENT DOCUMENTS

| | | |
|---|---|---|
| WO | WO 99/60956 | 12/1999 |
| WO | WO 00/49977 | 8/2000 |
| WO | WO 01/17464 | 3/2001 |
| WO | WO 2004/019828 | 3/2004 |
| WO | WO 2004/026186 | 4/2004 |
| WO | WO 2004/054479 | 7/2004 |

OTHER PUBLICATIONS

International Search Report for PCT/US2002/018572, Dec. 16, 2002, 3 pages.

International Search Report for PCT/US2006/019254, Mar. 19, 2007, 1 page.

Written Opinion for PCT/US2006/019254, Mar. 19, 2007, 3 pages.

International Preliminary Report on Patentability for PCT/US2006/019254, Nov. 30, 2007, 1 page.

International Search Report for PCT/US06/31379, May 3, 2007, 1 pg.

International Search Report for PCT/US2003/040086, Jul. 16, 2004, 1 page.

International Search Report for PCT/US2007/061972, Nov. 14, 2007, 1 page.

\* cited by examiner

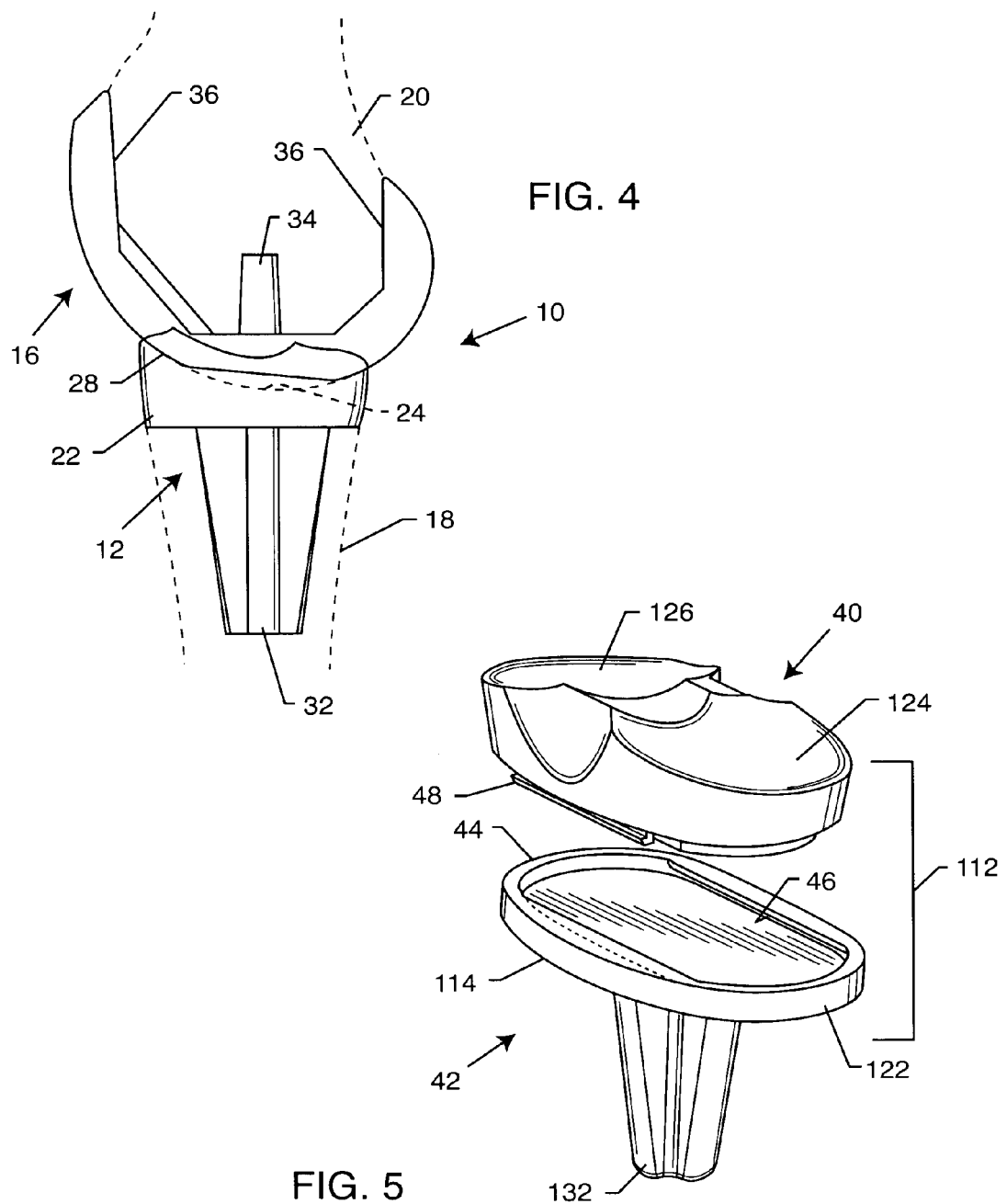

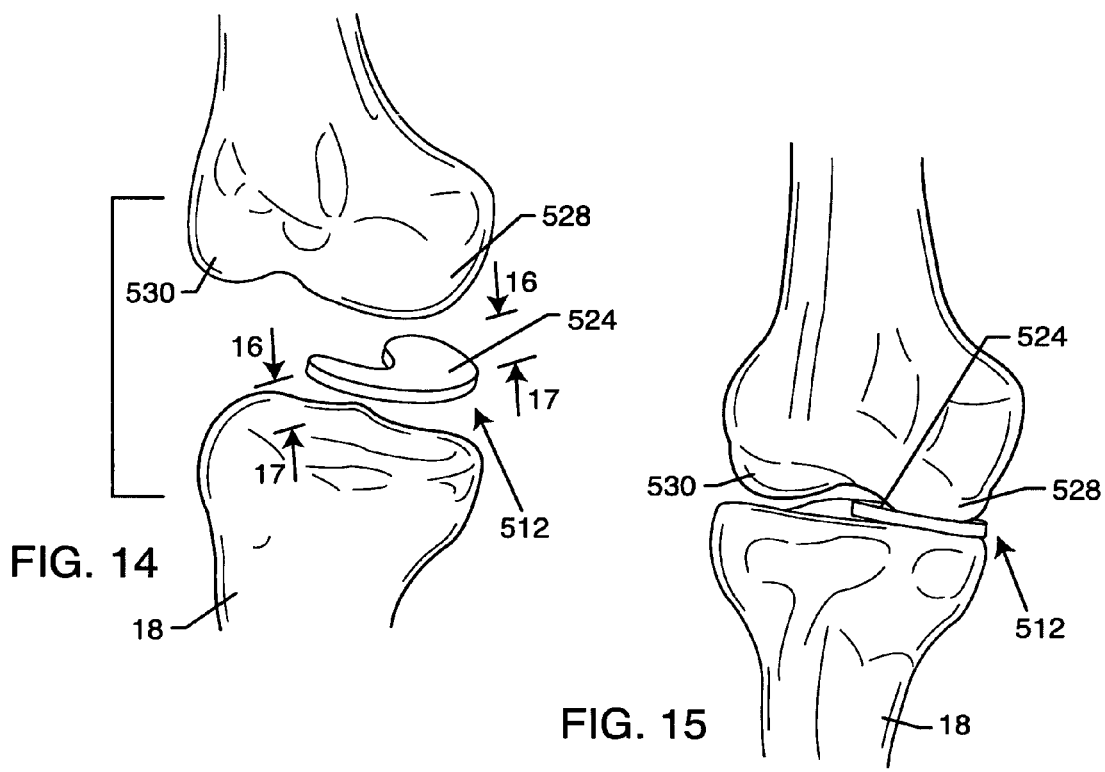
FIG. 14
FIG. 15
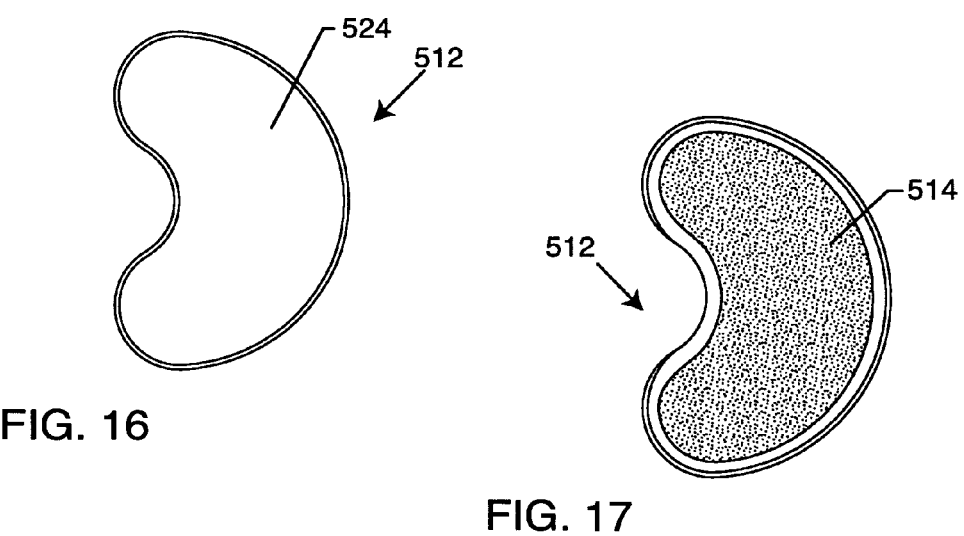
FIG. 16
FIG. 17

KNEE PROSTHESIS WITH CERAMIC TIBIAL COMPONENT

This application is a continuation-in-part of copending U.S. Ser. No. 10/987,415, filed Nov. 12, 2004, which is a division of U.S. Ser. No. 10/171,376, filed Jun. 13, 2002, now U.S. Pat. No. 6,881,229, issued Apr. 19, 2005, which in turn claims the benefit of U.S. Provisional Application 60/289,669, filed May 8, 2001.

This application is also a continuation-in-part of copending U.S. Ser. No. 11/040,477, filed Jan. 20, 2005, which is a continuation-in-part of U.S. Ser. No. 10/137,106, filed Apr. 30, 2002, now U.S. Pat. No. 6,846,327, issued Jan. 25, 2005, which in turn claims the benefit of U.S. Provisional Application 60/287,824, filed May 1, 2001.

In addition, this application is a continuation-in-part of U.S. Ser. No. 11/139,280, filed May 27, 2005 now abandoned.

BACKGROUND OF THE INVENTION

This invention relates generally to improvements in knee prostheses, particularly with respect to an improved tibial component constructed from a relatively hard and relatively high strength ceramic material. The ceramic tibial component includes at least one generally articulation surface designed for direct bearing engagement by and articulation against an associated femoral articulation surface having a generally convex or condylar shape. The ceramic tibial component is design for ultra low wear over an extended service life, and further permits elimination of a conventional polymer-based bearing insert and undesirable wear debris problems associated therewith.

Knee prostheses generally comprise a tibial component adapted for fixation to an appropriately resected upper end of the patient's tibia. Such tibial components have generally been formed from a biocompatible metal material such as cobalt chrome, titanium, stainless steel, or from polymer-based materials. The tibial component thus provides a strong and durable prosthetic base structure for supporting a polymer-based bearing insert which in turn defines a pair of upwardly presented, generally concave bearing seats for articulatory engagement with a corresponding pair of generally convex or condylar-shaped articulation surfaces at the lower end of the patient's femur. These femoral articulation surfaces can be defined by natural femoral bone surfaces, or alternately by condyle surfaces on a reconstructed or prosthetic femoral component affixed to the patient's femur. Such femoral components have generally been formed from a biocompatible metal material such as cobalt chrome, titanium, stainless steel, zirconium, zirconium oxide and ceramic materials such as alumina, zirconia and zirconia-toughened alumina (ZTA).

The polymer-based bearing insert is formed typically from a high density or ultra high molecular weight polyethylene (PE) material, which has been shown in various specific compositions to accommodate smooth and relatively low-wear articulation relative to the femoral surfaces. However, clinical studies have shown that significant wear debris can be generated and released by the polymeric bearing insert over a period of time, and further that a principle contributing factor to implant failure is osteolysis attributable at least in part to the presence of such polymer-based wear debris. More particularly, such studies have shown that PE wear debris released into peri-implant tissues appears to elicit a deleterious biological reaction, incorporating foreign body giant cell and macrophage cell responses leading to undesirable bone resorption, with eventual loosening and failure of the prosthetic implant. As a result, alternative prosthesis constructions have proposed improvements in and to the polymer-based bearing insert, such as the use of highly cross-linked polyethylene materials. Other alternative prostheses have been proposed using rigid-on-rigid components, such as ceramic-on-ceramic or metal-on-metal, thereby eliminating the polymer-based bearing insert and wear debris associated therewith. Bearing couples in the knee joint have been limited to metal-on-polymer or ceramic-on-polymer.

In general, ceramic knee prosthesis components have shown promise for use in a ceramic-on-ceramic or alternately in a ceramic-on-metal articulating interface, thereby completely eliminating the polymer-based bearing insert. Such prosthesis constructions, when formed with a good surface finish and conformal surface geometry, have demonstrated a relatively low coefficient of friction and resultant substantial reduction in component wear in comparison with ceramic-polymer or metal-polymer articulatory interfaces. However, the major limitation on the use of ceramic components particularly such as alumina-based ceramic materials has been an unacceptably high rate of brittle fracture occurring within a post-surgical follow-up period ranging from a few months to several years. In this regard, ceramic materials generally exhibit relatively low toughness and are thus prone to brittle fracture.

U.S. Pat. No. 6,881,229 discloses an improved ceramic material for use in joint prostheses, such as knee prostheses, wherein a ceramic-on-ceramic or a ceramic-on-metal articulatory interface is defined. The improved ceramic material comprises a doped silicon nitride ($Si_3N_4$) having relatively high hardness, tensile strength, elastic modulus, lubricity, and fracture toughness. Specifically, the improved doped silicon nitride ceramic has a flexural strength greater than about 700 Mega-Pascal (MPa) and a fracture toughness greater than about 7 Mega-Pascal root meter ($MPam^{0.5}$). This high strength and high toughness doped silicon nitride ceramic achieves ultra-low wear over an extended service life, with dramatically reduced risk of brittle fracture.

In addition, U.S. Pat. No. 6,846,327 discloses improved ceramic materials for bone graft applications, wherein the ceramic material is designed to mimic structural characteristics of natural patient bone by including first and second regions of comparatively lower and higher porosity to respectively mimic natural cortical and cancellous bone structures. The preferred ceramic materials disclosed exhibit a flexural strength greater than about 500 Mega-Pascal (MPa) and a fracture toughness greater than about 5 Mega-Pascal root meter ($MPam^{0.5}$). In use, the relatively low porosity region of the ceramic material provides high structural strength and integrity, whereas the higher porosity region is suitable for bone ingrowth to achieve secure and stable implant affixation.

The present invention comprises an improved knee joint prosthesis particularly wherein the load-bearing tibial component thereof is constructed from an improved high strength and high toughness ceramic material as disclosed, e.g., in U.S. Pat. No. 6,881,229 and/or U.S. Pat. No. 6,846,327.

SUMMARY OF THE INVENTION

In accordance with the invention, an improved knee prosthesis includes a load-bearing tibial component constructed from a relatively high strength and high toughness ceramic material and defining at least one articulation surface for ultra-low wear articulation with a generally convex or condylar-shaped femoral articulation surface defined by a femoral prosthetic component or by natural patient bone. The ceramic tibial component is adapted for direct fixation relative to the patient's tibial bone, or alternately in the form of a tibial bearing insert component carried by a tibial baseplate member which is adapted in turn for fixation to tibial bone.

In one form, the ceramic tibial component comprises a monoblock structure defining at least one and preferably a pair of generally concave articulation surfaces or bearing seats formed by a ceramic material having relative high hardness and high fracture toughness, such as the doped silicon nitride ($Si_3N_4$) disclosed in U.S. Pat. No. 6,881,229 which is incorporated by reference herein. This high strength and high toughness doped silicon nitride ceramic achieves ultra-low wear over an extended service life, with dramatically reduced risk of brittle fracture, when articulated against femoral articulation surfaces of prosthetic materials such as biocompatible metal or ceramic, or when articulated against natural femoral bone. For example, the doped silicon nitride can comprise one or more dopants selected from the group consisting of yttrium oxide, magnesium oxide, strontium oxide, and alumina. The flexural strength was measured on standard 3-point bend specimens per American Society for Testing of Metals (ASTM) protocol method C-1161 and fracture toughness measured using single edge notched beam specimens per ASTM protocol method E399. The tibial ceramic monoblock structure further includes an underside region defined by a ceramic porous bone ingrowth surface for secure ingrowth affixation to natural tibial bone, such as the porous ceramic disclosed in U.S. Pat. No. 6,846,327 which is also incorporated by reference herein. An alternate form would be the attachment of the component to the natural tibial bone through cementation. The porous structure may allow for bone interdigitation. A further alternate method for cementation would not include a porous section and be replaced with a slot or pocket that will receive the cement and may or may not include undercut features for tensile strength.

In one alternative preferred form of the invention, the ceramic tibial component comprises a tibial bearing insert constructed from a ceramic material (as described above) having relatively high hardness and high fracture toughness properties. This ceramic tibial bearing insert in configured for mounting in a fixed or partially mobile manner onto a tibial baseplate member which is adapted in turn for fixation to the patient's tibial bone. The tibial baseplate member may be constructed from ceramic material, preferably such as the above-described material forming a bearing platform defined by relatively high hardness and high toughness ceramic in combination with an underside region defined by a ceramic porous bone ingrowth surface. Alternately, the tibial baseplate member may be constructed from a biocompatible metal. In one form, the tibial bearing insert may include a central upstanding stabilizer post of the general type described in U.S. Pat. No. 5,116,375.

In another alternative form, the ceramic tibial component may comprise a meniscal bearing insert defining an upwardly presented articulation surface constructed from a ceramic material (as described above) having relatively high hardness and high fracture toughness, in combination with an underside region defined by a ceramic porous bone ingrowth surface suitable for ingrowth-fixation or bone cement fixation with a prepared region at the upper end of the patient's tibia. The hard and tough articulation surface typically defines a shallow upwardly concave bearing seat for articulating with a convex or condylar-shaped femoral articulation surface defined by a femoral prosthetic component or alternately by natural patient bone.

In each of the foregoing embodiments of the invention, the ceramic tibial component of the knee prosthesis permits the elimination of a polymer-based bearing insert, and thereby also permits elimination of post-surgical problems associated with polymer-based wear particles and debris. In addition, the ceramic tibial component provides for ultra low wear over an extended service life, substantially without incurring brittle fracture problems associated typically with ceramic prosthesis structures.

Other features and advantages of the present invention will become apparent from the following more detailed description, taken in conjunction with the accompanying drawings, which illustrate, by way of example, the principles of the invention.

BRIEF DESCRIPTION OF THE DRAWINGS

The accompanying drawings illustrate the invention. In such drawings:

FIG. 4 is a side elevation view of the knee prosthesis of FIGS. 1-3 in assembled relation and depicting patient femoral and tibial bones in dotted lines;

FIG. 5 is an exploded perspective view showing one alternative preferred form of the invention, including a ceramic tibial bearing insert adapted for assembly with a tibial base member;

FIG. 14 is an exploded perspective view illustrating a ceramic meniscal bearing component adapted for tibial fixation and interposed between a patient's femoral and tibial bones;

FIG. 15 is a perspective view showing the ceramic meniscal bearing component in assembled relation between the patient's femoral and tibial bones;

FIG. 16 is a top plan view of the meniscal bearing component, taken generally on the line 16-16 of FIG. 14; and FIG. 17 is a bottom plan view of the meniscal bearing component, taken generally on the line 17-17 of FIG. 14.

DETAILED DESCRIPTION OF THE PREFERRED EMBODIMENTS

Figure 1:
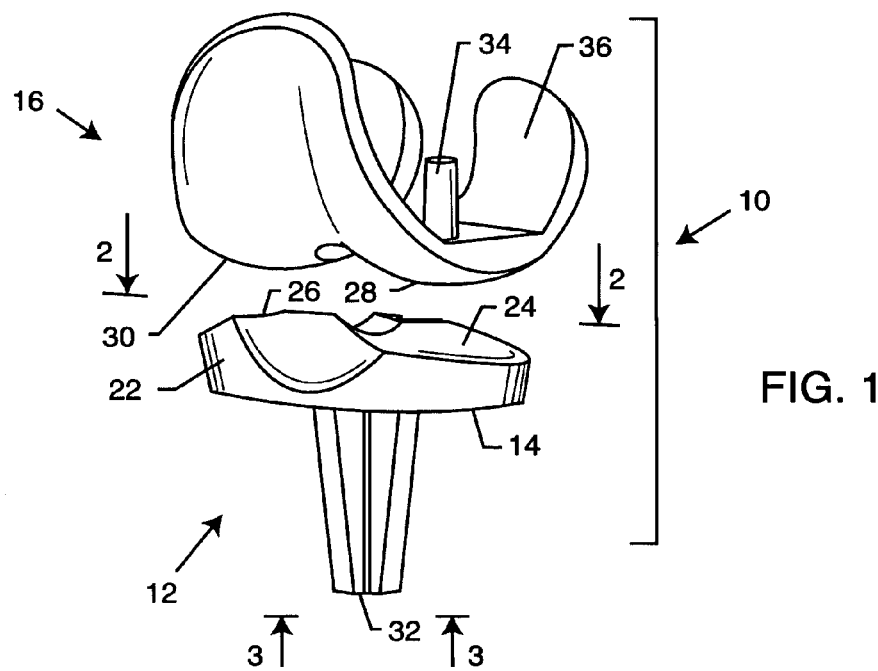
FIG. 1 is an exploded perspective view illustrating an exemplary knee prosthesis including a ceramic tibial component in accordance with one preferred form of the invention.

As shown in the exemplary drawings, an improved knee prosthesis referred to generally in one preferred form by the reference numeral 10 in FIGS. 1-4 includes a tibial component 12 constructed from a relatively hard and high strength ceramic material which may also incorporate a relatively porous ceramic bone ingrowth surface 14 (FIG. 3) for secure affixation to patient bone. The ceramic tibial component 12 is designed for articulation with a femoral prosthesis 16 (FIGS. 1 and 4) which may be constructed from a hard and high strength material such as a compatible and preferably identical ceramic material, or a biocompatible metal material, or alternately for articulation with natural patient femoral bone surfaces. The resultant ceramic-on-ceramic, or ceramic-on-metal, or ceramic-on-bone articulatory interface beneficially exhibits ultra-low wear over an extended service life, while additionally permitting elimination of the traditional polymer-based bearing insert and wear debris problems associated therewith.

FIGS. 1 and 4 illustrate the knee prosthesis 10 including the ceramic tibial component 12 and the associated femoral component 16 for repairing or replacing the natural anatomical articulatory surfaces of the human knee joint. In this regard, the ceramic tibial component 12 comprises a monoblock structure having a size and shape for seated and secure affixation at the upper end of a resected tibial bone 18 (FIG. 4), whereas the femoral component 16 has a size and shape for similarly seated and secure affixation at the lower end of a resected femoral bone 20. In general, the tibial component 12 defines an upwardly presented platform 22 which is contoured to form a laterally spaced pair of upwardly presented, generally concave bearing seats 24 and 26. The bearing seats 24, 26 define shallow concave articulation surfaces for respective engagement by and combined sliding and rolling articulation with generally convex medial and lateral condyles 28 and 30 formed on the femoral component 16.

By constructing the articulatory surfaces or bearing seats 24, 26 on the tibial component 12 from a selected ceramic material having high flexural strength and high fracture toughness properties, the resultant articulatory interface with the femoral condylar surfaces beneficially exhibits ultra low wear over an extended service life. Importantly, the invention permits elimination of the traditional polymer-based bearing insert, such as a high density or high molecular weight polyethylene (PE) bearing insert or the like normally fitted between the tibial component 12 and the femoral condyle structures to accommodate smooth articulation between these components. In this regard, clinical studies have linked premature prosthesis failures to the generation and accumulation of polymer-based wear debris associated with such polymer-based bearing inserts. In addition, the use of polymer-based inserts inherently increases the vertical span of the overall prosthesis construct, thereby restricting its utility to use with larger bone patients capable of receiving the larger sized prosthesis.

The ceramic tibial component 12 is shown in one preferred form in FIGS. 1-4, in the form of a unitary or substantially monoblock configuration to include the upper platform 22 contoured to define the concave bearing seats 24, 26, and further to define a downwardly protruding fixation post 32. This fixation post 32 is desirably shaped to have a noncircular cross-sectional configuration, such as the radially winged construction as shown, for seated reception into a resected upper end of the patient's tibia 18 (FIG. 4). In addition, an underside surface of the upper platform 22 carries the ceramic porous bone ingrowth surface coating or lining 14. Persons skilled in the art will recognize that alternative structural fixation elements such as pegs and the like, which may or may not be centrally positioned, may be used, and further that alternative fixation techniques such as a cemented prosthesis-bone interface may be used.

The preferred ceramic material used for constructing the ceramic tibial component 12 of the present invention comprises a high flexural strength and high fracture toughness ceramic material particularly such as a doped silicon nitride ($Si_3N_4$) having relatively high hardness, tensile strength, elastic modulus, lubricity, and fracture toughness properties, as described in detail in U.S. Pat. No. 6,881,229 which is incorporated by reference herein. This doped silicon nitride ceramic material has a relatively high flexural strength greater than about 700 Mega-Pascal (MPa) and a relatively high fracture toughness greater than about 7 Mega-Pascal root meter ($MPam^{0.5}$). This high strength and high toughness doped silicon nitride ceramic achieves ultra-low wear over an extended service life, with dramatically reduced risk of brittle fracture.

Figure 3:
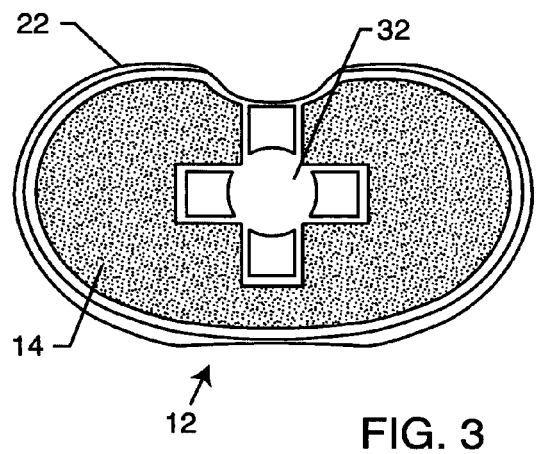
FIG. 3 is a bottom plan view of the ceramic tibial component, taken generally on the line 3-3 of FIG. 1.
Figure 2:
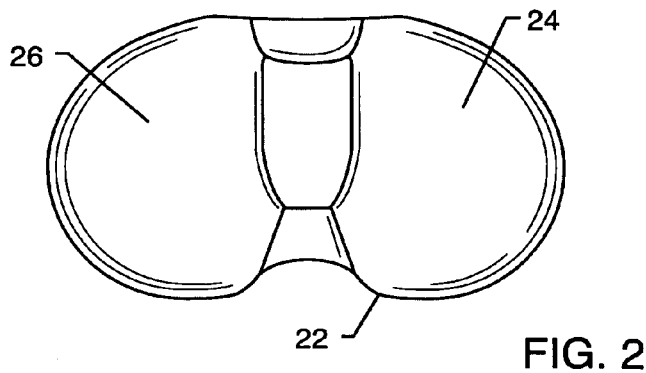
FIG. 2 is a top plan view of the ceramic tibial component, taken generally on the line 2-2 of FIG. 1.

This high strength and high toughness ceramic material is used to form a substrate for the ceramic tibial component 12. In this regard, such substrate structure has a relatively low porosity, and thus exhibits high density and high structural integrity generally consistent with and generally mimicking the characteristics of natural cortical bone lined with smooth lubricious articular cartilage. FIG. 3 further shows the ceramic porous bone ingrowth surface coating or lining 14 formed on the underside of the tibial platform 22, wherein this coating or lining exhibits a comparatively greater or higher porosity that is generally consistent with and generally mimics the characteristics of natural cancellous bone. As a result, this higher porosity surface coating or lining 14 provides an effective bone ingrowth surface for achieving secure and stable bone ingrowth affixation of the ceramic tibial component 12 with the patient's tibia 18.

While persons skilled in the art will recognize and appreciate that the specific material used for the bone ingrowth surface coating or lining 14 may vary, a preferred porous material comprises a ceramic porous ingrowth surface material. In this regard, U.S. Pat. No. 6,846,327 which is incorporated by reference herein discloses a ceramic bone graft component having relatively high flexural strength and relatively high toughness properties yet defining first and second regions of comparatively lower and higher porosity to respectively mimic natural cortical and cancellous bone structures. These regions of different porosity may be unitarily constructed or otherwise integrated into a common or monolithic ceramic component having a variable porosity gradient. In a preferred form, the ceramic tibial component 12 has a porosity gradient ranging from about 2% to about 80% by volume, with the higher porosity region having a porosity in the range of from about 30% to about 80% by volume, and with overall pore sizes ranging from about 50 microns to about 1,000 microns. In use, the relatively low porosity region of the ceramic material provides a dense and hard structure with high structural strength and integrity, whereas the higher porosity or less dense region is suitable for bone ingrowth to achieve secure and stable implant affixation.

U.S. Pat. No. 6,846,327 discloses a preferred alumina-zirconia ceramic material having a zirconia composition of about 10% to about 20% by volume, with either yttria stabilized zirconia (about 2.5 to about 5 mol % yttria in zirconia) or ceria stabilized zirconia (about 2.5 to about 15 mol % ceria in zirconia) for the zirconia phase. The resultant ceramic material exhibits a highly desirable combination of high flexural strength (greater than about 500 MPa) and high fracture toughness (greater than about 5 $MPam^{0.5}$). Such alumina-zirconia based ceramic material may be employed in the present invention for the ceramic tibilar component cup 12, although the stronger and tougher silicon nitride ($Si_3N_4$) ceramic as described in U.S. Pat. No. 6,881,229 is preferred.

Accordingly, in the preferred form, the ceramic tibial component 12 is constructed predominantly from relatively low porosity ceramic material having the desired high strength and high toughness properties, such as the doped silicon nitride ($Si_3N_4$) material described in the above-referenced U.S. Pat. No. 6,881,229. The ceramic tibial component 12 further includes the comparatively higher porosity bone ingrowth surface 14, formed preferably from a higher porosity ceramic material as described in the above-referenced U.S. Pat. No. 6,846,327, extending over a substantial area of the underside of the upper platform 22. This relatively high porosity bone ingrowth surface 14 is preferably formed integrally with the low porosity substrate, although persons skilled in the art will understand that the bone ingrowth surface 14 may be separately applied as a surface coating or lining.

The femoral component 16 shown in FIGS. 1 and 4 is constructed in the most preferred form from a ceramic material that is compatible with the ceramic tibial component material. In this regard, a preferred material for the femoral component 16 comprises a matching or identical high strength and high toughness ceramic material corresponding with the ceramic tibial component 12, as disclosed in U.S. Pat. No. 6,881,229. Alternately, the femoral component 16 may be constructed from a biocompatible metal material, preferably such as a cobalt chrome alloy as disclosed in the above-referenced U.S. Pat. No. 6,881,229, although other biocompatible metals may be used. In either configuration, the femoral component 16 defines the downwardly convex condyles 28, 30 forming articulating surfaces for engaging the bearing seats 24, 26 on the tibial component 12. In addition, an upper side of the femoral component 16 (in either ceramic or metal form) may incorporate one or more upstanding fixation posts 34 and/or one or more regions carrying a porous bone ingrowth surface or coating 36. In a ceramic embodiment, the femoral component 16 may comprise a monoblock or substantially unitary structure including a low porosity substrate having high strength and toughness properties defining the condyles 28, 30, in combination with one or more higher porosity regions defining the bone ingrowth surface or surfaces 36, as described in the above-referenced U.S. Pat. No. 6,846,327. Or, persons skilled in the art will recognize and appreciate that the ceramic tibial component 12 may be used in a partial knee prosthesis wherein the tibial component is adapted to engage and articulate against the natural condylar structures at the lower end for the patient's femur.

FIGS. 5-13 depict further alternative preferred forms of the ceramic tibial component of the present invention. For sake of convenience and ease of description, components shown in FIGS. 5-13 which correspond in structure and/or function to those shown and described in FIGS. 1-4 are identified by common reference numerals increased by a factor of 100.

Figure 6:
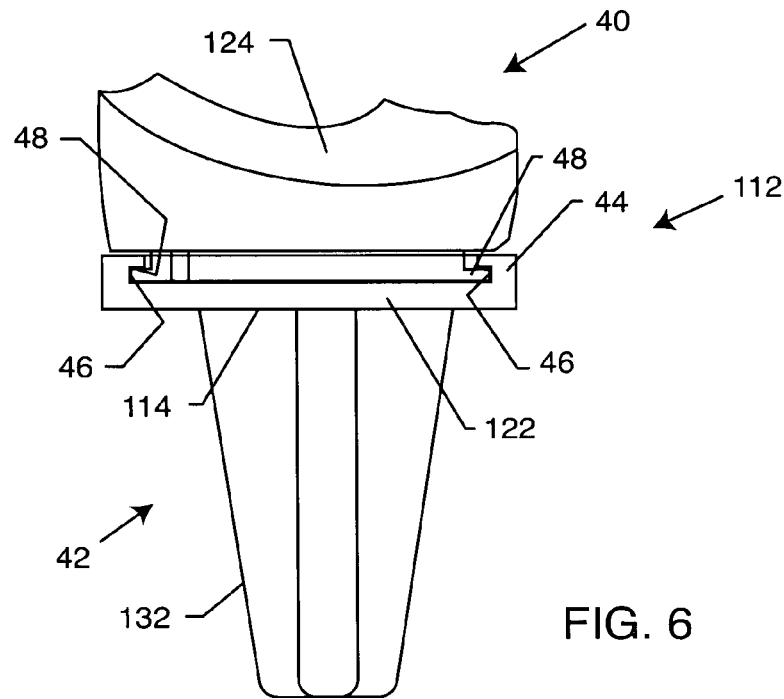
FIG. 6 is a side elevation view showing the tibial bearing component and base member of FIG. 5 in assembled relation.

FIGS. 5-6 depict a modified ceramic tibial component 112 including an upper ceramic bearing insert 40 defining a pair of upwardly presented, substantially concave bearing seats 124 and 126, and adapted for assembly with a lower tibial baseplate member 42. In this embodiment of the invention, the lower baseplate member 42 defines a tibial platform 122 at an upper end thereof, in combination with a downwardly protruding fixation post 132. In addition, an underside surface of the tibial platform 122 may incorporate a porous bone ingrowth surface or coating 114 similar to that shown and described in FIG. 3. The upper side of the platform 122 is lined by a short upstanding peripheral rim 44 which includes undercuts 46 (FIG. 6) at the anterior and posterior sides of the platform 122 for receiving and engaging lock ribs 48 formed on the bearing insert 40 to seat and retain the bearing insert 40 in assembled relation with the baseplate member 42.

In one preferred form, the ceramic bearing insert 40 is constructed from a selected high strength and high toughness ceramic material suitable for extended service life with ultra low wear when articulated with an associated ceramic or metal femoral component (not shown in FIGS. 5-6) or with natural femoral bone 20 (also not shown in FIGS. 5-6). A preferred ceramic material is again disclosed in U.S. Pat. No. 6,881,229. The associated baseplate member 42 is constructed from a biocompatible metal suitable for snap-fit engagement of the ceramic ribs 48 on the bearing insert 40 with the undercut rim 44 on the baseplate member 42. Alternately, if desired, the bearing insert 40 and baseplate member 42 may both be constructed from the same or compatible ceramic materials, with the snap-fit ribs 48 being constructed from a suitable deformable material mounted onto the bearing insert 40.

Figure 7:
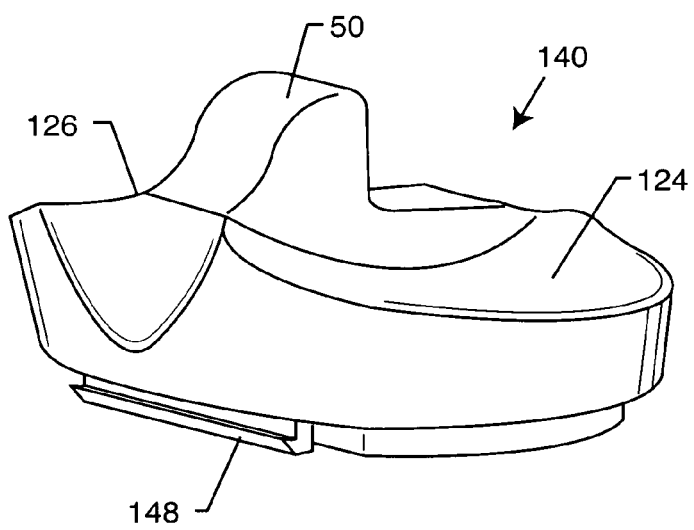
FIG. 7 is a perspective view illustrating an alternative configuration for the ceramic tibial bearing component.

FIG. 7 illustrates a modified bearing insert 140 corresponding with the bearing insert 40 shown and described in FIGS. 5-6, but further incorporating an upstanding central stabilizer post 50 projecting upwardly a short distance from a generally central location disposed between the two concave bearing seats 124, 126. This stabilizer post 50 provides additional stabilization of a reconstructed knee joint, particularly when used in combination with a femoral component of the type shown and described in U.S. Pat. No. 5,116,375 which is incorporated by reference herein. A pair of lower snap-fit ribs 148 are provided for mounting of the modified bearing insert 140 onto a tibial baseplate member 42 (FIGS. 5-6). Persons skilled in the art will further appreciate that the stabilizer post 50 shown in FIG. 7 may be incorporated into the monoblock tibial component 12 shown in FIGS. 1-4, or otherwise incorporated into any one of the various embodiments disclosed herein.

Figure 8:
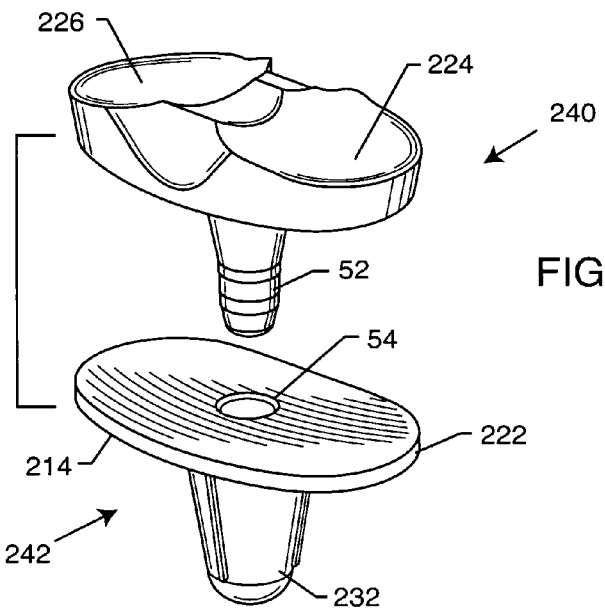
FIG. 8 is an exploded perspective view depicting a further alternative preferred form of the invention, including a ceramic tibial bearing component adapted for assembly with a tibial baseplate member.
Figure 9:
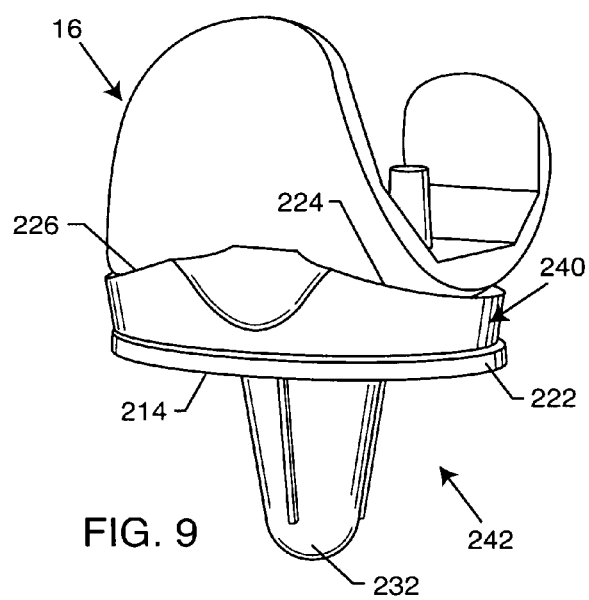
FIG. 9 is a perspective view showing the tibial bearing component and baseplate member of FIG. 8 in assembled relation, and further depicted in assembled relation with a femoral component for the knee prosthesis.
Figure 10:
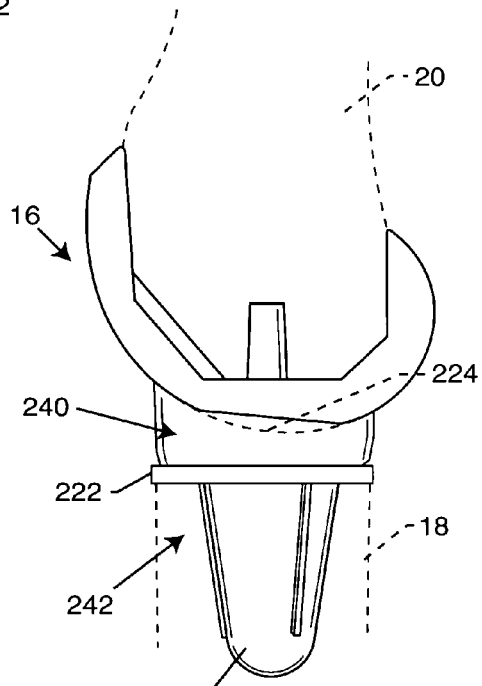
FIG. 10 is a side elevation view of the knee prosthesis illustrated in FIG. 9.

FIGS. 8-10 show a further alternative embodiment of the invention, wherein an upper ceramic bearing insert 240 is assembled with a lower tibial baseplate member 242. In this version of the invention, the upper bearing insert 240 is shaped to define the upwardly presented, generally concave bearing seats 224, 226, and further includes a downwardly extending central bearing post 52. This bearing post 52 is sized and shaped for slide-fit reception into an upwardly open bore 54 formed centrally within the underlying baseplate member 242 to extend downwardly within a fixation post 232. A tibial platform 222 is carried at the upper end of the baseplate member 242 and may incorporate a porous bone ingrowth surface 214 on an underside surface thereof.

The tibial baseplate member 242 is affixed to the upper end of the patient's resected tibia 18 (FIG. 10). The bearing insert 240 is assembled with the baseplate member 242 by slide-fit reception of the bearing post 52 into the open bore 54. In this position, the platform 222 provides stable support for a generally planar underside surface of the bearing insert 240, thereby permitting the bearing insert 240 to rotate about a central axis of the bearing post 52 during knee joint articulation. In this regard, FIGS. 9-10 show a femoral component 16 in articulatory engagement with the bearing insert 240, which is supported in turn upon the platform 222 of the lower baseplate member 242.

Figure 11:
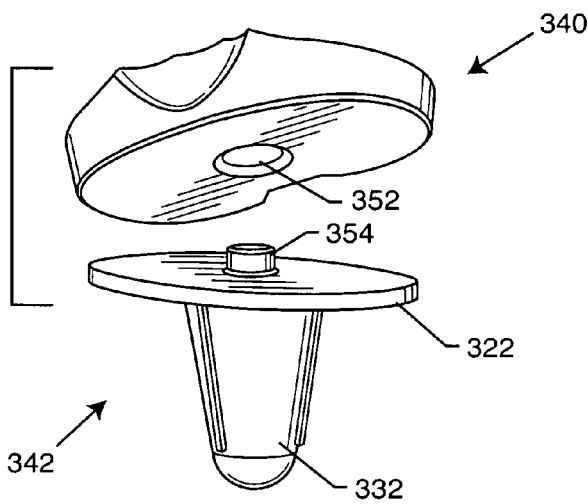
FIG. 11 is an exploded perspective view showing one alternative preferred configuration for the tibial bearing component and baseplate member of FIGS. 8-10.
Figure 12:
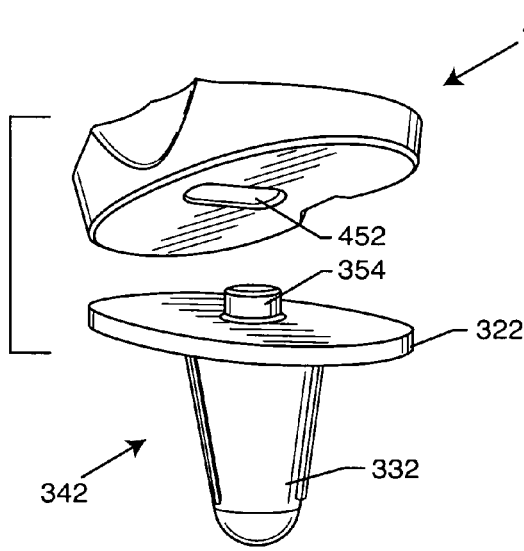
FIG. 12 is another perspective view showing another alternative preferred configuration for the tibial bearing component and baseplate member of FIGS. 8-10.
Figure 13:
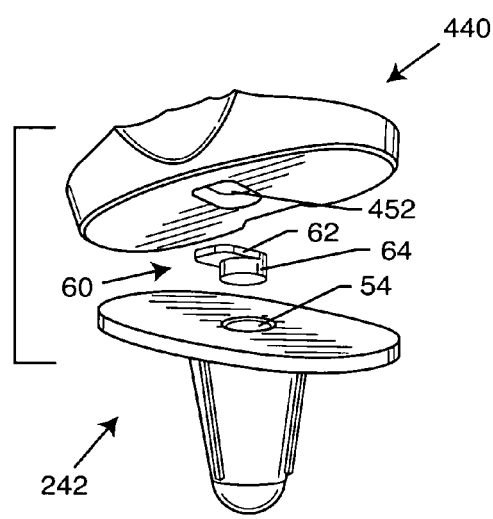
FIG. 13 is a further perspective view showing a further alternative preferred configuration for the tibial bearing component and baseplate member of FIGS. 8-10.

FIG. 11 shows a modification of the embodiment depicted in FIGS. 8-10, wherein the rotary support for an upper bearing insert 340 is replaced by a shallow bore 352 formed in the underside of the bearing insert 340 for slide-fit reception of a short peg 354 upstanding centrally from a platform 322 of a lower tibial baseplate member 342 including a central fixation post 332. FIG. 12 shows a further variation of the embodiment of FIG. 11, wherein the shallow bore formed in the underside of an upper bearing insert 440 comprises a slot 452 elongated in the fore-aft or anterior-posterior direction. The slot 452 is adapted to receive the upstanding peg 352 on the underlying tibial baseplate member 342 of the type shown and described in FIG. 11. FIG. 13 illustrates a further variation of FIG. 12 wherein a key 60 includes an elongated head 62 for seating within the slot 452, and a cylindrical body 64 for seating within an open bore 54 in the underlying tibial baseplate 242 of the type shown and described in FIGS. 8-10.

In these versions, FIG. 11 accommodates rotary displacement of the bearing insert 340 relative to the baseplate member 342 when the peg 354 is rotatably seated within the bore 352, but prevents relative movement between the assembled components when the peg 354 is press-fit mounted into the bore 352. In FIG. 12, the assembled components accommodate a combination of rotary and/or anterior-posterior shifting movement of the bearing insert 440 relative to the tibial baseplate member 342. Finally, the key 60 in FIG. 13 effectively prohibits relative movement of the slotted bearing insert of FIG. 12, when the key body 64 is press-fit mounted into the bore 54 of the baseplate member 242 of FIGS. 8-10. Alternately, rotary mounting of the key body 64 within the baseplate member bore 54 accommodates a combined rotation and translation between the assembled components.

In each of the embodiments depicted in FIGS. 8-13, the bearing insert is desirably formed from the high strength and high toughness ceramic material suitable for extended service life with ultra low wear when articulated with an associated ceramic or metal femoral component or with natural femoral bone 20. The preferred ceramic material again comprises the ceramic material disclosed in U.S. Pat. No. 6,881,229. The associated baseplate member is preferably constructed from the same or compatible ceramic material, or from a suitable biocompatible metal. In either form, ceramic or metal, the platform 22, 122, 322 defined by the baseplate member desirably includes the porous bone ingrowth surface formed on the underside thereof. In the ceramic configuration, a preferred baseplate member construction comprises the dual porosity ceramic material as described in the above-referenced U.S. Pat. No. 6,846,327, with the low porosity region defining a structural load bearing substrate and the higher porosity region defining the integral bone ingrowth surface.

FIGS. 14-17 show another alternative preferred form of the invention, wherein a modified ceramic tibial component 512 is provided in the form of a prosthetic meniscal bearing. This meniscal bearing 512 is sized and shaped for affixation to an suitably prepared and/or resected upper end region of the tibia 18, and defines an upwardly presented and preferably shallow concave bearing seat 524 for articulation with an adjacent femoral condyle surface, such as articulation with a natural bone condyle 528 as viewed in FIGS. 14-15. It will be recognized and understood, however, that the meniscal bearing component 512 may be used for articulation with a femoral prosthesis 16 of the type shown and described in FIGS. 1, 3 and 9-10. The underside surface of the meniscal bearing component 512 includes a porous bone ingrowth surface or coating 514 (FIG. 17) for ingrowth-affixation to the prepared tibia 18. While a single meniscal bearing component 512 is shown in FIGS. 14-15, it will be understood that a pair of such bearing components having suitable sizes, shapes and thicknesses may be provided for respectively articulating with the pair of condyles 528 and 530, or with corresponding condylar surfaces on a femoral prosthesis.

The meniscal bearing component 512 and particularly the bearing seat 522 is constructed from a selected high strength and high toughness ceramic material suitable for extended service life with ultra low wear. Once again, a preferred ceramic material is disclosed in U.S. Pat. No. 6,881,229. The underside bone ingrowth surface 514 of the bearing component 512 is desirably formed as an integral portion but with a higher porosity suitable for ingrowth affixation to patient bone, as disclosed in U.S. Pat. No. 6,846,327.

A variety of further modifications and improvements in and to the knee prosthesis of the present invention will be apparent to persons skilled in the art. For example, where ceramic articulation surfaces are specified, persons skilled in the art will recognize and appreciate that such ceramic surfaces may comprise a surface portion of a monolithic ceramic structure, or alternately comprise a ceramic coating carried by a non-ceramic substrate, such as a composite structure in the form of a metallic substrate having a ceramic coating thereon. One such exemplary composite structure comprises a metal alloy substrate having an integral ceramic articulation surface thereon, such as the implantable material marketed by Smith & Nephew, Inc. of Memphis, Tenn. under the name Oxinium. Accordingly, no limitation on the invention is intended by way of the foregoing description and accompanying drawings, except as set forth in the appended claims.

What is claimed is:

1. A knee prosthesis, comprising:
   a tibial component having a size and shape adapted for seated affixation to an upper end of a prepared tibia in a patient, said tibial component defining at least one upwardly presented bearing seat forming an articulation surface having a size and shape for articulatory engagement with a generally convex articulation surface formed on a mating femoral component;
   said articulation surface of said bearing seat being formed from a doped silicon nitride ceramic having a flexural strength greater than about 700 Mega-Pascal (MPa) and a fracture toughness greater than about 7 Mega-Pascal root meter (MPam$^{0.5}$), wherein said doped silicon nitride comprises one or more dopants selected from the group consisting of yttrium oxide, magnesium oxide, strontium oxide, and alumina.

2. The knee prosthesis of claim 1 further including a porous bone ingrowth surface on an underside of said tibial component for bone ingrowth affixation of said tibial component with the prepared patient tibia.

3. The knee prosthesis of claim 2 wherein said bone ingrowth surface comprises a ceramic bone ingrowth surface.

4. The knee prosthesis of claim 3 wherein said tibial component comprises a ceramic material having a variable porosity gradient defining a relatively low porosity first region defining said at least one bearing seat, and a comparatively higher porosity second region defining said ceramic bone ingrowth surface, said first and second regions being integrally formed.

5. The knee prosthesis of claim 4 wherein said ceramic material has a porosity gradient ranging from about 2% to about 80% by volume, with said higher porosity region having a porosity in the range of from about 30% to about 80% by volume.

6. The knee prosthesis of claim 5 wherein said ceramic material has pores formed therein with a pore size ranging from about 50 microns to about 1,000 microns.

7. The knee prosthesis of claim 1 wherein said generally convex articulation surface on said mating femoral prosthesis comprises a femoral condyle defined by a femoral prosthesis.

8. The knee prosthesis of claim 7 wherein said convex articulation surface of said femoral prosthesis is formed from a material selected from the group consisting of biocompatible ceramic and metal materials.

9. The knee prosthesis of claim 7 wherein said articulation surfaces of said femoral prosthesis and said tibial component are formed from the same doped silicon nitride ceramic.

10. The knee prosthesis of claim 1 wherein said tibial component has a monoblock ceramic structure.

11. The knee prosthesis of claim 1 wherein said tibial component comprises a bearing insert mounted on a tibial baseplate member, said at least one bearing seat being formed on said bearing insert, and said tibial baseplate member being adapted for seated affixation to an upper end of a prepared tibia in a patient.

12. The knee prosthesis of claim 11 wherein said bearing insert is movably mounted on said tibial baseplate member.

13. The knee prosthesis of claim 11 wherein said bearing insert is snap-fit mounted on said tibial baseplate member.

14. The knee prosthesis of claim 11 wherein said tibial baseplate member is formed from a material selected from the group consisting of biocompatible ceramic and metal materials and combinations thereof.

15. The knee prosthesis of claim 14 wherein said tibial baseplate member comprises a ceramic material having a variable porosity gradient defining a structural load bearing and relatively low porosity first region, and a comparatively higher porosity second region defining a bone ingrowth surface, said first and second regions being integrally formed.

16. The knee prosthesis of claim 11 wherein said articulation surface of said bearing insert and said tibial baseplate member are formed from the same doped silicon nitride ceramic.

17. The knee prosthesis of claim 1 wherein said at least one bearing seat comprises a pair of laterally spaced, generally upwardly concave bearing seats.

18. The knee prosthesis of claim 17 wherein said tibial component further includes a stabilizer post protruding upwardly from a position disposed generally between said pair of bearing seats.

19. The knee prosthesis of claim 1 wherein said tibial component comprises a meniscal bearing insert.

20. A knee prosthesis, comprising:
a tibial component having an underside surface including means for seated affixation to an upper end of a prepared tibia in a patient, said tibial component further defining at least one upwardly presented bearing seat forming an articulation surface having a size and shape for articulatory engagement with a generally convex articulation surface formed on a mating femoral component;
said tibial component being a monoblock formed from doped silicon nitride ceramic having a flexural strength greater than about 700 Mega-Pascal (MPa) and a fracture toughness greater than about 7 Mega-Pascal root meter (MPam$^{0.5}$), wherein said doped silicon nitride comprises one or more dopants selected from the group consisting of yttrium oxide, magnesium oxide, strontium oxide, and alumina.

21. The knee prosthesis of claim 20 wherein said affixation means comprises a porous bone ingrowth surface on said underside surface of said tibial component.

22. The knee prosthesis of claim 21 wherein said doped silicon nitride ceramic has a variable porosity gradient defining a relatively low porosity first region defining said at least one bearing seat, and a comparatively higher porosity second region defining said ceramic bone ingrowth surface, said first and second regions being integrally formed.

23. The knee prosthesis of claim 20 wherein said at least one bearing seat comprises a pair of laterally spaced, generally concave bearing seats.

24. The knee prosthesis of claim 20 wherein said tibial component comprises a meniscal bearing insert.

25. A knee prosthesis, comprising:
a tibial baseplate member having an underside surface including means for seated affixation to an upper end of a prepared tibia in a patient;
a tibial bearing insert carried by said baseplate member, said tibial bearing insert defining at least one upwardly presented bearing seat forming an articulation surface having a size and shape for articulatory engagement with a generally convex articulation surface formed on a mating femoral component;
said articulation surface of said tibial bearing insert being formed from a doped silicon nitride ceramic having a flexural strength greater than about 700 Mega-Pascal (MPa) and a fracture toughness greater than about 7 Mega-Pascal root meter (MPam$^{0.5}$), wherein said doped silicon nitride comprises one or more dopants selected from the group consisting of yttrium oxide, magnesium oxide, strontium oxide, and alumina.

26. The knee prosthesis of claim 25 wherein said affixation means comprises a porous bone ingrowth surface on said underside surface of said tibial baseplate member.

27. The knee prosthesis of claim 25 wherein said tibial baseplate member is formed from a material selected from the group consisting of biocompatible ceramic and metal materials.

28. The knee prosthesis of claim 27 wherein said tibial baseplate member comprises a ceramic material having a variable porosity gradient defining a relatively low porosity first region defining a load bearing structure, and a comparatively higher porosity second region defining said bone ingrowth surface, said first and second regions being integrally formed.

29. The knee prosthesis of claim 25 wherein said articulation surface of said tibial bearing insert and said tibial baseplate member are formed from the same doped silicon nitride ceramic.

30. The knee prosthesis of claim 25 wherein said at least one bearing seat comprises a pair of laterally spaced, generally concave bearing seats.

31. The knee prosthesis of claim 25 wherein said tibial bearing insert is movably mounted on said tibial baseplate member.

32. The knee prosthesis of claim 25 wherein said tibial bearing insert is snap-fit mounted on said tibial baseplate member.

33. The knee prosthesis of claim 25 wherein said tibial bearing insert and said tibial baseplate member cooperatively define an interengaging post and bore to accommodate relative rotary movement therebetween.

34. The knee prosthesis of claim 25 wherein said tibial bearing component and said tibial baseplate member cooperatively define an interengaging post and anterior-posterior elongated slot to accommodate relative rotary and anterior-posterior sliding movement therebetween.

35. The knee prosthesis of claim 25 wherein one of said tibial bearing component and said tibial baseplate member has an anterior-poster elongated slot formed therein, and the other of said tibial bearing component and said tibial baseplate member has a bore formed therein, and further including a key having an elongated head seated within said slot and a generally cylindrical body seated within said bore.

* * * * *